United States Patent [19]

de Rooij

[11] 3,997,607

[45] Dec. 14, 1976

[54] RECYCLING PROCESS FOR THE PREPARATION OF CYCLOHEXANONE OXIME

[75] Inventor: Abraham H. de Rooij, Geleen, Netherlands

[73] Assignee: Stamicarbon B.V., Geleen, Netherlands

[22] Filed: Apr. 24, 1975

[21] Appl. No.: 571,396

Related U.S. Application Data

[63] Continuation-in-part of Ser. Nos. 542,045, Jan. 17, 1975, and Ser. No. 564,085, April 1, 1975, said Ser. No. 542,045, is a continuation-in-part of Ser. No. 95,389, Dec. 4, 1970, and Ser. No. 95,318, Dec. 4, 1970, said Ser. No. 564,085, is a continuation-in-part of Ser. No. 422,711, Dec. 7, 1973, and Ser. No. 422,713, Dec. 7, 1973.

[30] Foreign Application Priority Data

Apr. 26, 1974 Netherlands .................... 7405630

[52] U.S. Cl. .................................... 260/566 A
[51] Int. Cl.$^2$ .................................. C07C 131/04
[58] Field of Search ........................... 260/566 A

[56] References Cited

FOREIGN PATENTS OR APPLICATIONS

| 441,674 | 6/1972 | Australia | 260/566 A |
| 944,362 | 3/1974 | Canada | 260/566 A |
| 1,283,894 | 8/1972 | United Kingdom | 260/566 |
| 1,283,496 | 7/1972 | United Kingdom | 260/566 A |

Primary Examiner—Gerald A. Schwartz
Attorney, Agent, or Firm—Cushman, Darby & Cushman

[57] ABSTRACT

An improved cyclic process for producing cyclohexanone oxime is provided wherein the circulating reaction medium is subjected to a heat treatment, at a temperature of at least 120° C in the presence of nitrous gases, and at an absolute pressure of over 1 atmosphere, as it circulates between the oxime synthesis zone and the hydroxylamines synthesis zone. Cyclohexanone oxime is a valuable commercial commodity e.g. for the preparation of nylon-6 via ε-caprolactam.

8 Claims, 1 Drawing Figure

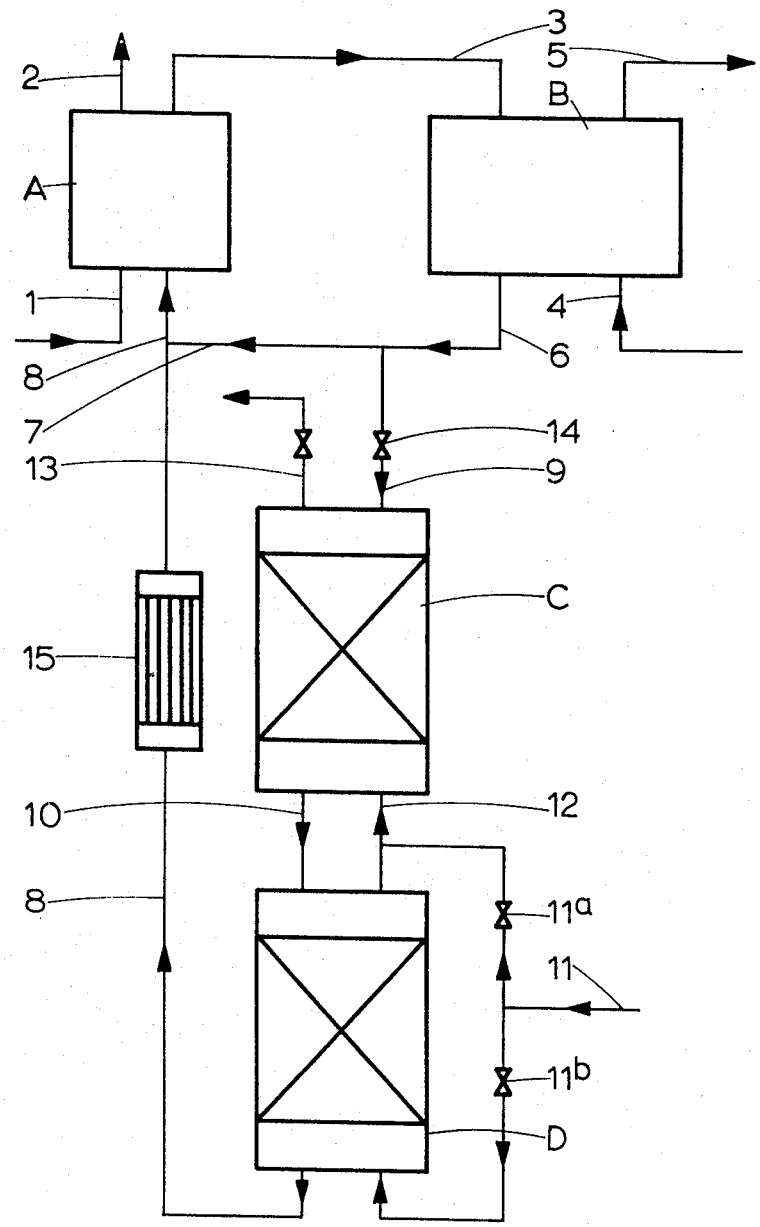

3,997,607

RECYCLING PROCESS FOR THE PREPARATION OF CYCLOHEXANONE OXIME

CROSS REFERENCE TO RELATED APPLICATIONS

This application is a continuation-in-part application of Ser. No. 542,045, filed Jan. 17, 1975, which is relied upon and incorporated herein by reference. This application is also a continuation-in-part application of U.S. Pat. Application, Ser. No. 564,085, filed Apr. 1, 1975 in the name of the inventor for IMPROVED CYCLIC PROCESS FOR PREPARING AND WORKING UP A HYDROXYL-AMMONIUM SALT SOLUTION, which is also relied upon and incorporated herein by reference. Said U.S. Pat. Application Ser. No. 542,045 (filed Jan. 17, 1975) is in turn a continuation-in-part application of both U.S. Pat. Applications Ser. No. 95,389 and Ser. No. 95,318, both filed on Dec. 4, 1970. U.S. Pat. Application Ser. No. 564,085, filed Apr. 1, 1975, in the name of the inventor, for IMPROVED CYCLIC PROCESS FOR PREPARING AND WORKING UP A HYDROXYL-AMMONIUM SALT SOLUTION, is a continuation-in-part application of (a) Ser. No. 422,711, filed Dec. 7, 1973, which in turn is a Rule 60 application of Ser. No. 114,172, filed Feb. 10, 1971 and now abandoned, and (b) Ser. No. 422,713, filed Dec. 7, 1973, which is in turn is a Rule 60 application of Ser. No. 114,171, filed Feb. 10, 1971, now abandoned.

BACKGROUND OF THE INVENTION

The invention relates to a cyclic process for the preparation of cyclohexanone oxime from cyclohexanone and a hydroxyl-ammonium salt which includes the steps of preparing a solution of the required hydroxyl-ammonium salt and of reacting the hydroxyl-ammonium salt with cyclohexanone.

British Patent Specification No. 1,283,894 discloses a process wherein a buffered aqueous reaction medium showing an acid reaction is recycled between (1) a zone for the synthesis of hydroxyl-ammonium ions by means of molecular hydrogen, and (2) a zone for the synthesis of cyclohexanone oxime, in which the resulting hydroxyl ammonium ions react with cyclohexanone to form cyclohexanone oxime. In this process the buffering action of the reaction medium is due to the presence of buffer acids and salts thereof, in the reaction medium, e.g., phosphoric acid and/or bisulphate as a buffer acid with a phosphate and/or sulphate, respectively, as a buffer salt.

Before the recycled aqueous reaction medium is passed into the zone for the synthesis of hydroxyl-ammonium salt, it is enriched with the required nitrate ions either by addition of nitric acid or by absorption of nitrous gases in the aqueous reaction medium, in which instance nitric acid is formed in situ.

The catalyst used for the reduction of the nitrate ions is, for instance palladium or a palladium-platinum alloy, and the catalyst support is, for instance, carbon or aluminum oxide. The carrier is loaded with catalyst so that the supporting material contains, e.g., 5–20% by weight of catalyst.

The aforementioned reference discloses that the activity of such a catalyst is adversely affected if the catalyst is contaminated with organic substances, such as the cyclohexanone to be converted or the cyclohexanone oxime product. To overcome this problem, the reference teaches reducing the total content of dissolved ketone and oxime in the recycling liquid to a value of at most 0.02% by weight by heating the recycling liquid at a temperature of at least 50° C in the presence of nitrous gases, before the recycling liquid is passed into the zone for the synthesis of the hydroxyl-ammonium salt. The required amount of nitrous gases can then be adjusted by adding nitrous gases or an alkali nitrite to the recycling liquid.

This known process for lowering the ketone and oxime content has the following drawbacks:

1. A large amount of recycling liquid per ton of final product must be subjected to said heat-treatment.
2. If an ammonium salt is used as a buffer salt in the recycling liquid, the ammonium-ion content may become too low, because the known reaction of ammonium ions with nitrous gases with simultaneous formation of nitrogen at a temperature of over about 40° C appears to proceed at least equally as quickly as the reaction in which the catalyst poisons are rendered harmless.
3. As any hydroxyl-ammonium salt present during the heat-treatment may decompose, the overall process efficiency in using an excess amount of hydroxyl-ammonium salt in order to obtain cyclohexanone oxime with the lowest possible cyclohexanone content is not always controllable.

SUMMARY OF THE INVENTION

It has now been found that the above drawbacks can be obviated, and yet the activity and selectivity of the catalyst can be retained, by heating and recycling liquid partly and/or periodically at a temperature of at least 120° C and under pressure in contact with nitrous gases, before it is passed into the zone for the synthesis of hydroxyl-ammonium salt. If the heat treatment is applied to only part of the recycling liquid, e.g. 10%, at atmospheric pressure and at a lower temperature, e.g. 50°–80° C, (1) the desired effect of the improvement of the invention is not realized, and (2) reduction of the activity and selectivity of the catalyst to a considerable extent, apparently, occurs. Examination of this adverse effect on the catalyst disclosed that the cyclohexanone oxime still contained in the untreated part of the recycling liquid is reduced to cyclohexylamine, which, when subjected to a heat treatment at a temperature of below 120° C, decomposes and is converted into catalyst poisons.

The relation between the temperature of the heat treatment in question and the cyclohexylamine content of an aqueous solution that is comparable to the recycling liquid is apparent from the results of a number of experiments at various temperatures, which are compiled in the table below. In each experiment nitrous gases (obtained by mixing 28 parts by volume of nitrogen monoxide and 72 parts by volume of air) were passed through 1500 grams of aqueous solution for about 2 hours at the rate of 7 liters per minute. The aqueous solution was contained in an autoclave under autogenous pressure (based on atmospheric pressure at room temperature) and contained 1 mole of orthophosphoric acid, 1.1 moles of mono-ammonium phosphate, 2 moles of ammonium nitrate, and 0.4 gram of cyclohexyl amine per kilogram at the start of each experiment. The amount of nitrous gases passed through was considerably larger than was required for the decomposition of the ammonium ions according to the reaction:

$$2 NH_4^+ NO + NO_2 \rightarrow 2 N_2 + 3 H_2O + 2 H^+$$

in which the required nitrogen dioxide was formed by oxidation of the nitrogen monoxide with the oxygen of the air in the nitrous gases used.

Table

| Temp. in °C | cyclohexyl amine and catalyst poisons formed therefrom, in % of original amount of cyclohexyl amine | % of original amount of cyclohexyl amine converted into dicarboxylic acids | % of original amount of cyclohexyl amine discharged as carbon dioxide |
| --- | --- | --- | --- |
| 40 | 98 | 2 | 0 |
| 60 | 94 | 4.5 | 1.5 |
| 80 | 85 | 14 | 1 |
| 100 | 53 | 36 | 11 |
| 110 | 20 | 60 | 20 |
| 125 | 0 | 65 | 35 |
| 150 | 0 | 55 | 45 |

As appears from the table, the cyclohexyl amine has completely decomposed at the temperatures 125° and 150° C. The carbon dioxide formed from the cyclohexyl amine is discharged as a gas, while the dicarboxylic acids formed from the cyclohexyl amine, together with the cyclohexanone oxime, are removed from the recycling liquid by extraction. Thus, it is an object of the invention to remove from the reaction medium those organic substances which will contaminate the catalyst employed to reduce the nitrate ions.

DETAILED DESCRIPTION OF THE INVENTION

The chemical reactions taking place during the successive steps of the process for the preparation of cyclohexanone oxime wherein the reaction medium comprises a solution containing phosphoric acid, are as follows:

1. formation of hydroxyl-ammonium salt in the hydroxyl-ammonium salt synthesis zone:

$$2 H_3PO_4 + NO_3^- + 3 H_2 \rightarrow NH_3OH^+ + 2 H_2PO_4^- + H_2O$$

2. formation of cyclohexanone oxime in the oximation zone:

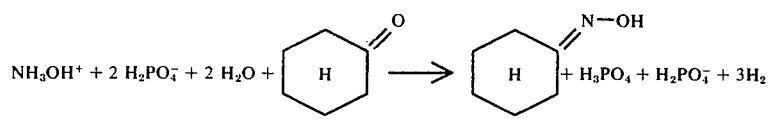

3. make-up, in the form of $HNO_3$, of nitrate ions consumed, after the oxime formed has been separated from the reaction mixture:

$$H_3PO_4 + H_2PO_4^- + HNO_3 \rightarrow 2 H_3PO_4 + NO_3^-$$

The cyclic process for the preparation of oximes from hydroxylamine of a hydroxyl-ammonium salt is carried out in an acidic, buffered, aqueous reaction medium containing buffer acids such as phosphoric acid, bisulfate or buffer salts derived from these acids and mixtures thereof. The reaction medium is circulated between a hydroxyl-ammonium salt synthesis zone, where nitrate ions, which have been added to the reaction medium, are catalytically reduced with molecular $H_2$ to hydroxylamine, and an oximation zone where a ketone is added to react with the hydroxyl-ammonium salt to produce an oxime. The nitrate ions consumed in the hydroxyl-ammonium synthesis zone are added to the circulating reaction medium just before the reaction medium is introduced into the hydroxyl-ammonium salt synthesis zone. The nitrate ions are generally added in the form of nitric acid of approximately 60 weight percent.

The nitrate ions in the hydroxylamine synthesis zone are first converted into hydroxylamine which in turn reacts with the available buffer acid in the reaction medium, forming the corresponding hydroxyl-ammonium salt. The resulting solution obtained, containing hydroxyl-ammonium salt, is withdrawn from the hydroxylamine synthesis zone and circulated to the oximation zone, where the hydroxyl-ammonium salt, together with a ketone, which is also fed to the oximation zone, forms the corresponding oxime, with liberation of acid. The oxime is removed from the oxime synthesis zone. The reaction medium withdrawn from the oxidation zone contains small amounts of oxime and ketone. This aqueous reaction medium is then returned to the hydroxylamine synthesis zone.

Following the make-up of $HNO_3$, a solution is again available which, after removal of both the water formed by the reaction and the water introduced with the nitric acid make-up, will, theoretically, have the same composition as the initial solution used for the formation of hydroxyl-ammonium salt. This solution is then circulated back to the hydroxylamine synthesis zone. The reduction of the nitrate ions in the hydroxyl-amine synthesis zone is accomplished in the presence of a catalyst; usually a palladium catalyst is used although a palladium-platinum alloy catalyst can be used. The palladium is suspended on a carrier material of carbon or aluminum oxide. The carrier material is usually loaded to a desired degree, for instance, 5–20 weight percent of palladium, based on the carrier.

Organic substances, such as the ketone which is to be converted into oxime, and the resulting oxime itself, have an adverse effect on the activity of the catalyst if allowed to come into contact with the catalyst. To prevent the catalyst from being poisoned by these compounds, the circulating reaction medium must be purged of the ketone and oxime contaminants prior to its entering the hydroxylamine synthesis zone. The ketone and oxime content of the reaction medium should preferably be reduced to a value of not more than 0.02% by weight before the reaction medium is recirculated to the hydroxylamine synthesis zone.

The invention is directed to a cyclic process for undertaking those three reactions. The cyclic process of the invention is directed to an improvement in a process which comprises recycling an acidic aqueous buffer reaction medium which contains an ammonium salt as the buffer salt from a zone in which the step of catalytically reducing nitrate ions to hydroxyl-ammonium ions (the acid salt of hydroxylamine) is undertaken to a zone in which said hydroxyl ammonium ions react with cyclohexanone to form cyclohexanone oxime, wherein the required amount of nitrate (ions) and cyclohexanone are fed to the respective zones and wherein cyclohexanone oxime is discharged from the zone in which it is produced. The improvement of the invention comprises heating at least a portion of that liquid which is recycled between the two aforementioned zones to a temperature of at least 120° C, at an absolute pressure which is greater than one pressure absolute and in the presence of nitrous gases, wherein heating is undertaken after the liquid has been discharged from the zone in which cyclohexanone oxime is synthesized and before the liquid is fed into that zone in which hydroxyl-ammonium salt is produced. This heating step can be undertaken periodically in the continuous process of recycling said liquid.

The temperature in the hydroxylamine synthesis zone ranges from about 40° to about 100° C, while the temperature in the oxime synthesis zone ranges from 40° to 90° C. These two zones may be maintained at atmospheric, sub-atmospheric or at elevated pressures.

The heat treatment according to the invention may be carried out at various temperatures over 120° C. The heat treatment, in accordance with the invention, is undertaken at elevated pressure. The elevated pressure is chosen, in relation to the temperature of the heat treatment, to maintain the recycled liquid in the liquid state. As the temperature chosen for heat treatment increases, it is obvious that correspondingly higher pressures will have to be used in order to keep the recycling liquid to be treated in the liquid state. For practical purposes it suffices to use temperatures not exceeding 175° C. At temperatures between 120° and 175° C the required pressure varies between about 1.1 and about 7 atmospheres gauge.

Periodic treatment of the whole volume of the recycling liquid in the process according to the invention has the drawback that the required composition of the total recycling liquid is changed intermittently, which renders undertaking the recycling of the liquid through the two zones in a continuous way more complex. Thus, preferably part of the recycling liquid is always subjected to the heat treatment; e.g. 4–20% of the total recycling liquid. Suitably, an amount of 5–12% of the total recycling liquid is subjected to the heat treatment of the invention.

During the heat treatment according to the invention, the recycling liquid should be contacted with nitrous gases. The terminology "nitrous gases" here denotes gas containing nitrogen dioxide, in which the nitrogen dioxide can be formed in situ, e.g. from nitrogen monoxide and oxygen, and in which also an inert gas, such as, e.g., nitrogen, may be present. The nitrogen dioxide can optionally be admixed with nitrogen monoxide. Preferably nitrous gases which contain 0.4 – 2.5 moles of nitrogen monoxide per mole of nitrogen dioxide are employed. A mixture of this type can be obtained by known methods by catalytic combustion of ammonia with air or by reaction of the acid, e.g. the acid recycling liquid, with an alkali nitrite.

The amount of nitrous gases which is contacted with the recycling liquid to be treated should naturally be greater than the amount consumed in the decomposition of the ammonium ions according to the above-mentioned reaction equation. Very suitable results can be obtained in practice if the partial nitrous pressure (sum of partial pressures of nitrogen dioxide and nitrogen monoxide) has a value which is higher than the nitrous-gas pressure of nitric acid at a temperature corresponding to the temperature at which the heat treatment is effected. At temperatures ranging between 120° and 175° C, this nitrous-gas pressure exceeds 0.15 atmosphere.

An embodiment of the process according to the invention is shown in a simplified way in the Drawing.

DESCRIPTION OF THE DRAWING

In this FIGURE, A and B denote the zone for the synthesis of hydroxyl-ammonium salt and the zone for the synthesis of cyclohexanone oxime, respectively. Hydrogen is fed through conduit 1 to zone A, in which a catalyst containing palladium is suspended in the reaction medium. Hydrogen that has not reacted and other vent gases, if any, are removed through conduit 2. Through conduit 8, zone A is fed with the recycled reaction medium, which, after being enriched with hydroxyl-ammonium salt, is passed into zone B for the synthesis of cyclohexanone oxime through conduit 3. Cyclohexanone, which can optionally be dissolved in an organic solvent which is a solvent for cyclohexanone and cyclohexanone oxime (e.g. toluene, benzene, xylenes, cyclohexane and methylcyclopentane), is fed to zone B through conduit 4, while the resulting cyclohexanone oxime, optionally in solution in the organic solvent, is discharged through conduit 5. The recycling liquid is returned to the zone A for the synthesis of hydroxylamine through conduits 6, 7 and 8.

A part flow of the recycling process liquor is passed into a column C by way of control valve 14 and a conduit 9, and subsequently returned to the zone A for the synthesis of hydroxyl amine by way of conduit 10, reaction vessel D, a condensor 15, and conduit 8. Nitrous gases are fed to the system through conduit 11. The greater part of the amount of nitrous gases fed in are passed through valve 11a and conduit 12 into absorption column C, where they are absorbed at a comparatively low temperature, e.g. 40°–60° C with simultaneous formation of nitric acid. The remaining part of the amount of nitrous gases supplied through conduit 11 is passed, via valve 11b, into reaction vessel D, which is kept at an absolute pressure of at least 1 atmosphere and a temperature of over 120° C, e.g. 120°–175° C, and where the decomposition of the compounds that are poisonous to the catalyst is effected by the presence of nitrous gases. The amount of nitrous gases to be fed to the column C and the reaction vessel D can be controlled in a simple way by adjustment of the valves 11a and 11b. If so desired, the nitrous gases to be introduced into reaction vessel D may be absorbed separately, at a temperature below 60° C, in liquid from absorption column C, and the liquid enriched with nitrous gases which is so obtained be passed into the reaction vessel D. This vessel may then be designed to have a smaller size.

It is also possible to feed the total amount of nitrous gases to reaction vessel D. The amount of nitrous gases will then have to be such that a sufficiently large amount flows from reaction vessel D through conduit 12 to absorption column C in order to form the required amount of nitric acid. Non-absorbed gases are discharged through reducing valve 13.

The reaction products formed in reaction vessel D are mainly monocarboxylic and dicarboxylic acids which have no poisonous effect on the catalyst. The content of these compounds in the recycling liquid remains at a low level, as these compounds are largely removed through conduit 5 together with the cyclohexanone oxime formed. The invention is further elucidated by the following example.

EXAMPLE

In the continuous preparation of cyclohexanone oxime according to the diagram shown in the FIGURE, in which the catalyst used in zone A was palladium on coal with 10% by weight of palladium, the composition of the liquid flowing through conduit 6 (at the rate of 16.7 kilograms per hour) was:

$H_3PO_4$ = 1.13 moles per kilogram
$NH_4H_2PO_4$ = 1.01 moles per kilogram
$NH_4NO_3$ = 1.39 moles per kilogram
$(NH_3OH)_3PO_4$ = 0.02 mole per kilogram
$H_2O$ = 36.55 moles per kilogram The total amount of organic compounds contained in this liquid as impurities was 400 parts by weight per million, calculated as carbon. Of the total amount, 1 p.p.m. related to cyclohexanone oxime, 17 p.p.m. to cyclohexylamine, 80 p.p.m. to carboxylic acids, and 302 p.p.m. to unknown amine compounds.

An amount of about 6% of the liquid flow through conduit 6 was passed into absorption column C through control valve 14 and conduit 9, and subsequently into reaction vessel D by way of conduit 10. Through conduit 11 and the opened valve 11b, 740 liters/h of nitrous gases were passed into reaction vessel D and, subsequently, through conduit 12, into absorption column C. The gas supplied through conduit 11 had an absolute pressure of 6–7 atmospheres and its composition was:

5.2% by volume of NO
5.1% by volume of $NO_2$
10% by volume of $O_2$
79.9% by volume of $N_2$ The temperature in reaction vessel D was kept at 125° C by means of steam heating (not shown). The temperature in absorption column C was kept at about 40° C by means of a cooler (not shown). The absolute pressure in columns D and C was 6–7 atmospheres. The vent gas discharged through reducing valve 13 had the composition:

0.1% by volume of NO
0.005% by volume of $N_2O$
6.1% by volume of $O_2$
6.2% by volume of $H_2O$
87.6% by volume of $N_2$ The liquid discharged from reaction vessel D through conduit 8 contained:

$H_2O$ = 23 moles per kilogram
$HNO_3$ = 6.15 moles per kilogram
$H_3PO_4$ = 1.01 moles per kilogram In addition, this liquid contained 260 p.p.m. of organic compounds (calculated as carbon), 258 p.p.m. of which in the form of harmless carboxylic acids. Cyclohexanone oxime and cyclohexylamine could no longer be detected in this liquid.

What is claimed is:

1. In a cyclic process for producing cyclohexanone oxime, comprising recycling an acidic buffered aqueous reaction medium containing an ammonium salt as a buffer salt between a zone (A) for the synthesis of hydroxyl-ammonium salt, in which zone hydroxyl-ammonium ions are formed by catalytic reduction of nitrate ions and a zone (B) for the synthesis of cyclohexanone oxime, in which zone the resulting hydroxyl-ammonium ions react with cyclohexanone to form cyclohexanone oxime; wherein nitrate ions and cyclohexanone are fed to zones A and B, respectively, and wherein cyclohexanone oxime is discharged from zone (B); and wherein the said recycled reaction medium is treated after leaving zone (B) and before it is fed back into zone (A) to remove residual amounts of cyclohexanone and cyclohexanone oxime, the improvement consisting of heating at least a portion of said recycled liquid at a temperature of at least 120° C, in the presence of nitrous gases, and at an absolute pressure of over 1 atmosphere, after said recycled liquid has been discharged from zone (B) and before it is fed to the zone for the synthesis of hydroxy-ammonium salt (A).

2. The process according to claim 1, wherein 5 to 12% of the recycling liquid is subjected to said heat treatment, continuously.

3. In a cyclic process for producing cyclohexanone oxime, comprising recycling an acidic buffered aqueous reaction medium containing an ammonium salt as a buffer salt between a zone (A) for the synthesis of hydroxyl-ammonium salt, in which zone hydroxyl-ammonium ions are formed by catalytic reduction of nitrate ions and a zone (B) for the synthesis of cyclohexanone oxime, in which zone the resulting hydroxyl-ammonium ions react with cyclohexanone to form cyclohexanone oxime; wherein nitrate ions and cyclohexanone are fed to zones A and B, respectively, and wherein cyclohexanone oxime is discharged from zone (B); and wherein the said recycled reaction medium is treated after leaving zone (B) and before it is fed back into zone (A) to remove residual amounts of cyclohexanone and cyclohexanone oxime, the improvement consisting of heating at least a portion of said recycled liquid periodically at a temperature of at least 120° C, in the presence of nitrous gases, and at an absolute pressure of over 1 atmosphere, after said recycled liquid has been discharged from zone (B) and before it is fed to the zone for the synthesis of hydroxy-ammonium salt (A).

4. The process according to claim 1, wherein said nitrous gases comprise a nitrogen dioxide and nitrogen monoxide, wherein said nitrogen monoxide is present in an amount ranging from between 0.4 to 2.5 moles per mole of nitrogen dioxide.

5. The process according to claim 1, wherein only a portion of said recycled liquid is subjected to said heating step.

6. The process according to claim 5, wherein 20% of said recycling liquid is subjected to the heating step.

7. The process according to claim 5, wherein said heating step is undertaken periodically in the continuous process of recycling said liquid.

8. The process according to claim 3, wherein the whole volume of the recycling liquid is subjected to said heating step.

* * * * *